(12) United States Patent
Adkins

(10) Patent No.: US 7,111,371 B2
(45) Date of Patent: Sep. 26, 2006

(54) METHOD AND APPARATUS FOR PREVENTING LEAKAGE OF BODILY FLUIDS AND OTHER FLUIDS DURING EMBALMING TO PRESERVE THE DIGNITY OF THE DECEASED DURING MEMORIAL SERVICES

(76) Inventor: Thomas M. Adkins, 3309 E. Blackhawk Dr., Phoenix, AZ (US) 85024

( * ) Notice: Subject to any disclaimer, the term of this patent is extended or adjusted under 35 U.S.C. 154(b) by 234 days.

(21) Appl. No.: 10/459,083

(22) Filed: Jun. 11, 2003

(65) Prior Publication Data

US 2004/0064926 A1  Apr. 8, 2004

(51) Int. Cl.
*A01N 1/00* (2006.01)
(52) U.S. Cl. .................. 27/21.1; 27/22.1; 27/24.1
(58) Field of Classification Search ............ 27/1, 27/2, 7, 21.1, 22.1, 23.1, 24.1, 24.2; 411/395, 411/403–405, 407, 408, 426, 908; 5/606; 604/332, 337, 256; 600/32; 606/1, 213, 606/108, 185; 128/887
See application file for complete search history.

(56) References Cited

U.S. PATENT DOCUMENTS 5,431,655 A * 7/1995 Melker et al. ............... 606/79
6,654,991 B1 * 12/2003 Berry, Jr. ..................... 27/21.1

FOREIGN PATENT DOCUMENTS

EP        349955 A  *  1/1990

* cited by examiner

*Primary Examiner*—Tatyana Zalukaeva
*Assistant Examiner*—Melanie J. Hand
(74) *Attorney, Agent, or Firm*—Tod R. Nissle, P.C.

(57) ABSTRACT

An improved embalming method and apparatus functions to prevent leakage of bodily fluids and other fluids during embalming and to preserve the dignity of the deceased during memorial services. The improved embalming method and apparatus includes a trocar button, Calvarian clamp, ligature dispenser, defrigerant liquid, and an elevation device.

14 Claims, 14 Drawing Sheets

METHOD AND APPARATUS FOR PREVENTING LEAKAGE OF BODILY FLUIDS AND OTHER FLUIDS DURING EMBALMING TO PRESERVE THE DIGNITY OF THE DECEASED DURING MEMORIAL SERVICES

More particularly, the invention pertains to a method and apparatus to facilitate the closure of openings, bone cuts, and incisions made during the embalming of a deceased individual.

Deceased individuals have been embalmed and otherwise prepared for memorial services for many years. It appears however, that little has been done to improve many techniques used during embalming and that prior art techniques and apparatus have drawbacks that can produce results that interfere with, or at the worst, destroy the dignity that should be associated with a memorial service for a deceased individual.

During embalming, various openings are formed in the body of a deceased person. Catheters are inserted through skin and tissue to administer embalming fluid. Incisions are made. Bone cuts can be made.

In one procedure, the top 21 of the skull 23 is removed from the bottom 22 by cutting through the skull along a line 24 that extends around the skull. See FIG. 1. The top of the skull is then reattached using a conventional Calvarian clamp of the type illustrated in FIG. 3 and generally indicated by reference character 10. The clamp 10 includes steel plates 11 and 12 and externally threaded screw 13. Plate 11 includes a circular opening 15 through which the threaded portion 19 of screw 14 can freely slide. Opening 15 is, however, smaller than head 20 of screw 13. Plate 12 includes an internally threaded opening 16 through which portion 19 can not freely slide but which permits portion 19 to be turned through opening 16. Plates 11 and 12 include pointed feet that dig into skull bone to anchor plates 11 and 12 when the Calvarian clamp is mounted on the skull. In use, plates 11 and 12 are held parallel to and spaced apart from one another. Portion 19 is slidably inserted through opening 15 and is turned a short distance into internally threaded opening 16. The plates 11 and 12 are mounted on the edge 24 of the bottom portion 22 of the skull in the general position illustrated in FIG. 2. The edge 25 of the top 21 of the skull 23 is then downwardly moved in the direction of arrows E and inserted between plates 11 and 12. The end of a flat blade screwdriver is inserted in slot 14 of screw 13. The screwdriver is used to turn screw 13 such that portion 19 turns further through aperture 16 and draws plate 12 toward plate 11 and toward the inside of the skull. When portion 19 is turned a sufficient distance through aperture 16, plate 12 is pulled against the inside of the skull and plate 11 is pressed by the head of screw 13 against the outside of the skull. The foregoing procedure has disadvantages. First, the tip of the screwdriver tends to slide out of slot 14. Second, and more importantly, when the screwdriver is used to turn portion 19, portion 19 often will not thread through aperture 16. Instead, aperture 16 and plate 12 turn simultaneously with portion 19. Since plate 12 is inside the skull, it cannot readily be held. As a result, attempting to install securely a conventional Calvarian clamp can be unusually frustrating. In a worst case scenario, the clamp is not secured properly and the point at which the top of the skull is separated from the bottom of the skull can actually be discerned when the body of the deceased person is being viewed during a memorial service. Such an occurrence destroys the dignity of the deceased and of the service and should be avoided.

During another embalming procedure, a catheter is inserted through skin and tissue to administer embalming fluid to the circulatory system of a deceased individual. After the embalming fluid is administered, the catheter is withdrawn and the opening created in the skin and tissue by the catheter is closed by inserting and externally threaded "button" of the type illustrated in FIG. 9. The button in FIG. 9 is about one-half inch high and includes threads that generally have a height less than about one millimeter. These buttons have, like the conventional Calvarian clamp, been used for decades. One disadvantage of the button is that it can only be used in tissue openings having a size in a particular range and can not be readily used in openings that are smaller or larger. Another disadvantage of the button is that it tends to pop out and allow embalming and bodily fluids to leak from the deceased individual. A further disadvantage is that the button is inserted using the tool 32 illustrated in FIG. 11. The nubs 33 and 34 of the tool 32 are inserted and seated in openings 30 and 31. Handle 35 is manually grasped and turned and pressed against button 36 to turn button 36 into an opening in the skin and tissue of the deceased individual. If the tool 32 is tilted, one of numbs 33 can slide out of its receiving opening 30 or 31, in which case tool 32 no longer turns button 36.

Another prior art button 37 is illustrated in FIG. 10. Button 37 is longer than button 36. Button 36 typically is only about one-half inch long. Button 37 is more nearly about an inch long. The height of the threads of button 37 is, like the height of the threads on button 36, minimal. Button 37 includes a conical tip with a smooth outer surface 38. Button 37, like button 36 is not readily used in small openings. Button 37 includes a rib 41 bracketed by a pair of openings 39 and 40. Tool 32 is also used to install button 37. The rib 41 fits intermediate nubs 33 and 34. The shape and dimension of nubs 33 and 34 and of rib 41 can make rib 41 fit quite snugly between nubs 33 and 34 so that after button 37 is installed and an attempt is made to separate nubs 33 and 34 from rib 41, nubs 33 and 34 tend to maintain contact with rib 41 and to pull button 37 out of the opening formed in the skin and tissue of the deceased individual.

In a worst case scenario, when prior art buttons do not function properly, fluid can leak from the body of the deceased person and the fluid can be seen on clothing when the body of the deceased person is viewed during a memorial service.

Another procedure used during embalming is the use of ligature to suture closed incisions in the body. Ligature is spooled. The ligature typically is exposed. When the embalmer reaches for ligature, embalming fluids and bodily fluids on the embalmers gloves can contact and contaminate ligature spools.

Another problem encountered during embalming is administering embalming fluid to bodies that have been refrigerated. The cool temperature of the bodies can make administration of embalming fluid difficult.

Another problem encountered during embalming is the treatment of individuals whose skin has, for a variety of reasons, an unusual yellow color or other color.

Accordingly, it would be highly desirable to provide an improved embalming method and apparatus that would remedy the problems set forth above and that would function to maintain the dignity of the deceased.

Therefore, it is a principal object of the invention to provide an improved embalming method and apparatus.

A further object of the invention is to provide an improved embalming method and apparatus that would enable buttons used to seal openings in the body to be readily utilized in openings of various sizes, that would enable the button to be more readily controlled during insertion in the body, and that would reduce the likelihood that the button would be pulled from or pop out of a body opening after insertion.

Another object of the invention is to provide an improved e method and apparatus that would facilitate the use of Calvarian clamps to secure the top of the skull to the bottom of the skull.

Still a further object of the invention is to provide an improved ligature dispensing system that would reduce the risk that embalming fluid and bodily fluids would contaminate a ligature spool.

Still another object of the invention is to provide an improved embalming method and apparatus that would facilitate the embalming of bodies that have been refrigerated or otherwise cooled and that would facilitate the embalming of bodies have unusual skin or tissue coloring.

These and other, further and more specific objects and advantages of the invention will be apparent from the following detailed description of the invention, taken in conjunction with the drawings, in which.

Figure 1:
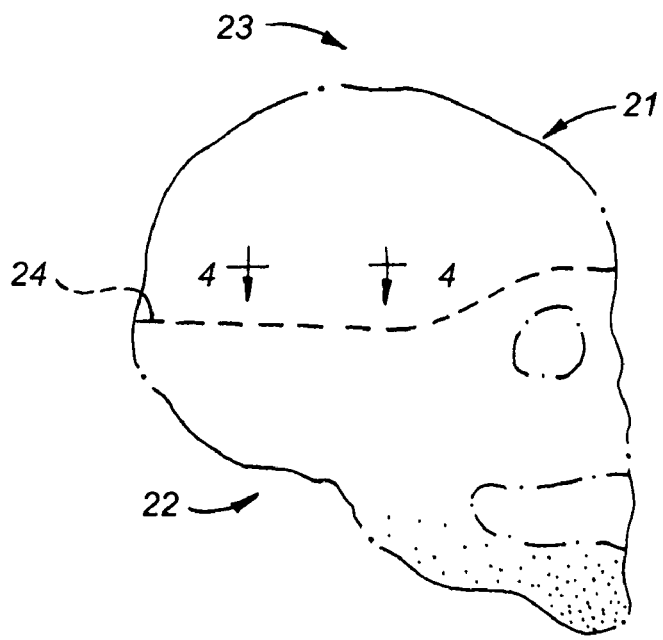
FIG. 1 is a side view illustrating a human skull.

Briefly, in accordance with my invention, I provide an improved embalming procedure. The procedure includes the steps of forming in the body of a deceased person an opening having a width of less than about one-half of an inch; providing a tapered button having a head and a neck with external threads formed thereon, the threads having a height greater than one millimeter and extending upwardly from the tip of said button; and, turning said button into said opening.

In another embodiment of my invention, I provide an improved embalming procedure. The procedure includes the steps of removing the top of the skull of a deceased person from the bottom of the skull; and, providing a clamp. The clamp includes a screw with a head and a neck and external threads formed on the neck; a first plate with a first opening formed therethrough to slidably receive the neck; a second plate with an internally threaded second opening formed therethrough to rotatably receive the neck such that the threads on the neck are turned through the second opening, the neck extending from the head first through the first opening and then through the second opening; and, a spring intermediate the head and the first plate. The procedure also includes the step of securing the top of the skull to the bottom of the skull with the clamp.

In a further embodiment of my invention, I provide an improved embalming procedure. The procedure includes the steps of making an incision in the body of a deceased person; and, providing a ligature dispensing system. The ligature dispensing system includes a container substantially enclosing a supply of ligature; an opening formed through the container to pull ligature from within the container; and, a cutter for severing a length of ligature pulled from within the container. The procedure also includes the steps of pulling ligature from the container and using the cutter to cut a length of ligature; and, using the length of ligature to suture at least a portion of the incision.

In another embodiment of my invention, I provide an improved procedure for embalming the body of a deceased person. The procedure includes the steps of placing the body on a top of a table, the body including legs, feet, ankles, a skull including a top and a bottom, a dermis, a vascular system, and an opening formed through the dermis, the opening having a width of less than about one-half of an inch; of positioning an elevation device adjacent the table, the elevation device including a support surface extending above said table such that the elevation device is prevented from contacting the top of the table; of elevating the legs of the body by placing the feet or ankles on the support surface; of removing the top of the skull from the bottom of the skull; and, of providing a clamp. The clamp includes a screw with a head and a neck and external threads formed on the neck; a first plate with a first opening formed therethrough to slidably receive the neck; a second plate with an internally threaded second opening formed therethrough to rotatably receive the neck such that the threads on the neck are turned through the second opening, the neck extending from the head first through the first opening and then through the second opening; and, a spring intermediate the head and the first plate. The method also includes the steps of securing the top of the skull to the bottom of the skull with the clamp; making a second opening in the body; and, providing a ligature dispensing system. The ligature dispensing system includes a container substantially enclosing a supply of ligature; an opening formed through the container to pull ligature from within the container; and, a cutter for severing a length of ligature pulled from within the container. The method also includes the steps of pulling ligature from the container and using the cutter to cut a length of ligature; of using the length of ligature to suture at least a portion of the second opening; of embalming the body at least in part by administering an aqueous solution of derefrigerant fluid in the vascular system of the body; of providing a tapered button having a head and a neck with external threads formed thereon, the threads having a height great than one millimeter and extending upwardly from the tip of said button; and, turning the button into the opening.

Turning now to the drawings, which depict the presently preferred embodiments of the invention for the purpose of illustrating the practice thereof and not by way of limitation of the scope of the invention, and in which like reference characters refer to corresponding elements throughout the several views, FIG. 1 illustrates a human skull 23 including a top 21, a bottom 22, and a line of demarcation 24 along which the skull 23 can be cut to separate the top 21 from the bottom 22.

Figure 3:
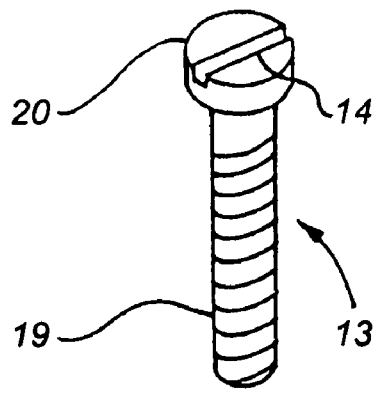
FIG. 3 is an exploded view illustrating a conventional Calvarian clamp.
Figure 3:
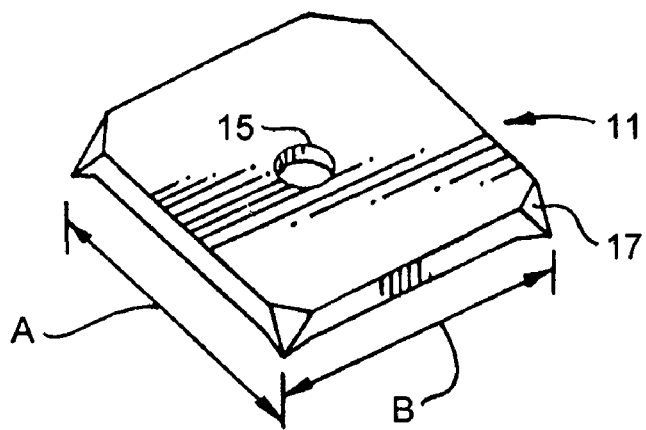
Figure 3:
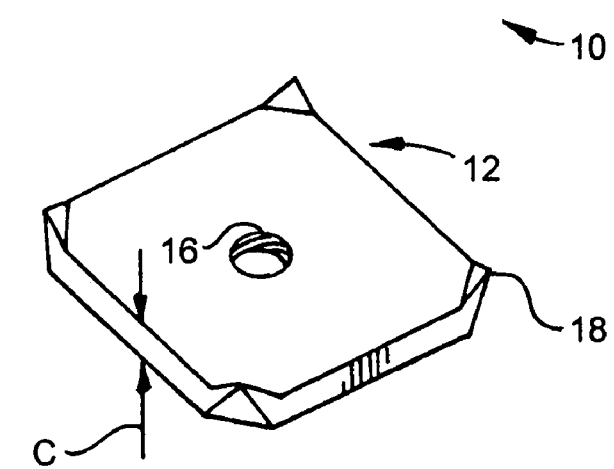

As noted earlier, FIG. 3 illustrates a conventional Calvarian clamp including screw 13, plate 11 and plate 12. Plate 11 includes aperture 15 shaped to slidably receive the externally threaded portion 19 of screw 13. Internally threaded aperture 16 in plate 12 is dimensioned such that portion 19 is rotatably turned through aperture 16. Apart from apertures 15 and 16, plates 11 and 12 are identical, although the shape of plate 11 can, if desired, differ from that of plate 12. The length A and width B of each plate 11 and 12 in a conventional Calvarian clamp is typically presently 17 mm, but in the practice of the invention these dimensions can vary as desired. The height C of each plate 11 and 12 in a conventional Calvarian clamp is presently 1.5 mm, but in the practice of the invention can vary as desired.

Figure 6:
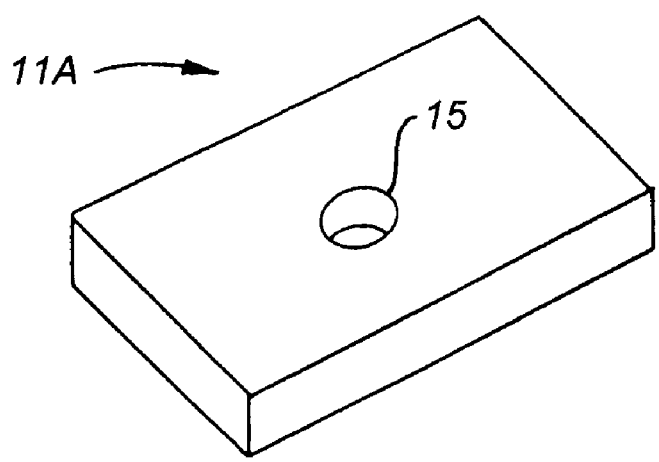
FIG. 6 is a perspective view illustrating an alternate plate shape in the Calvarian clamp of the invention.
Figure 7:
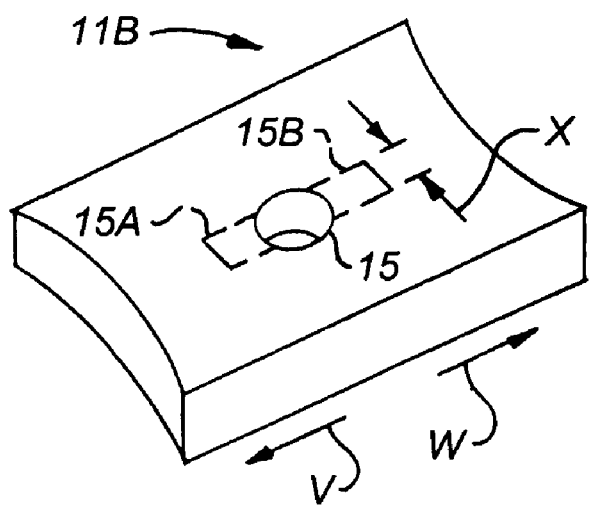
FIG. 7 is a perspective view illustrating another alternate plate shape in the Calvarian clamp of the invention.
Figure 8:
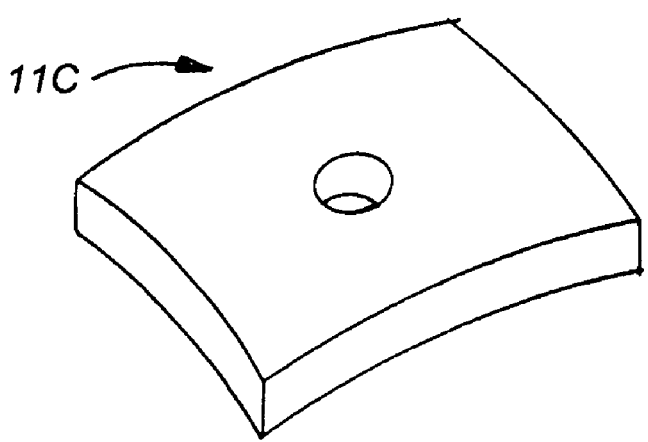
FIG. 8 is a perspective view illustrating still another alternate plate shape in the Calvarian clamp of the invention.
Figure 9:
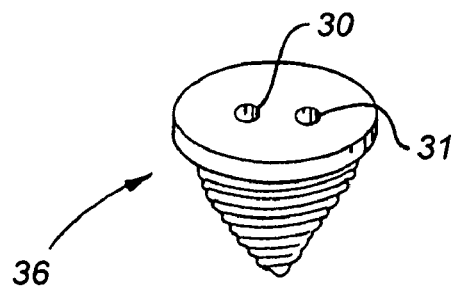
FIG. 9 is a perspective view illustrating a prior art button used during embalming to close an opening formed in the body of a deceased person.
Figure 11:
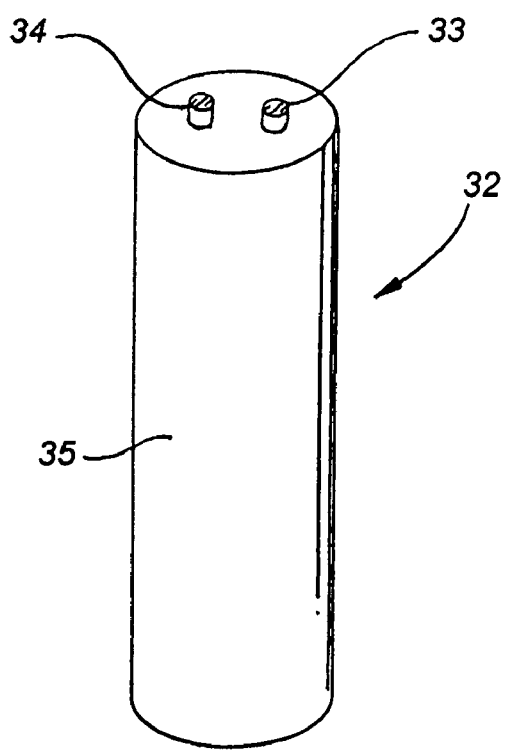
FIG. 11 is a perspective view illustrating the prior art tool used to insert the buttons of FIGS. 9 and 10.
Figure 10:
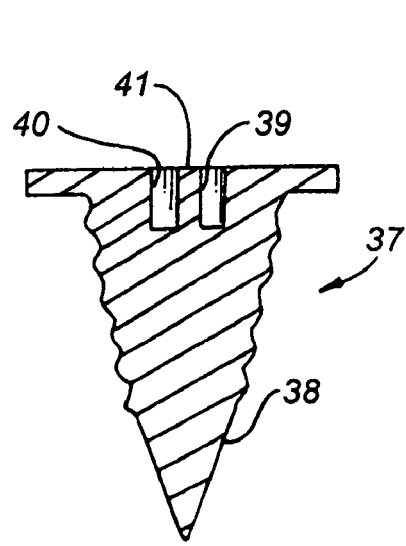
FIG. 10 is a side section view illustrating another prior art button used during embalming to close an opening formed in the body of a deceased person.
Figure 15:
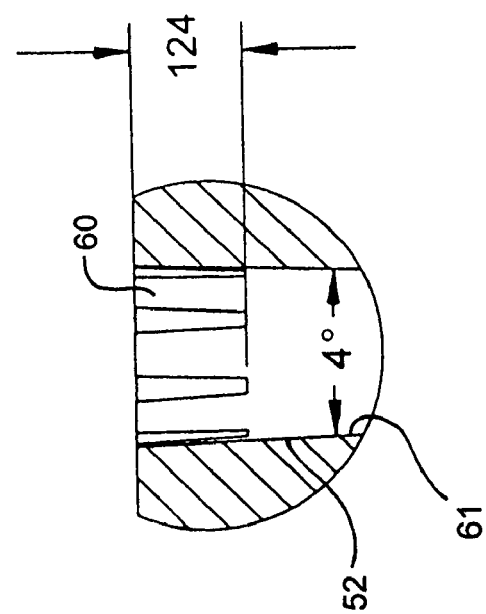
FIG. 15 is an enlarged view of the button of FIG. 14 illustrating further construction details thereof.
Figure 12:
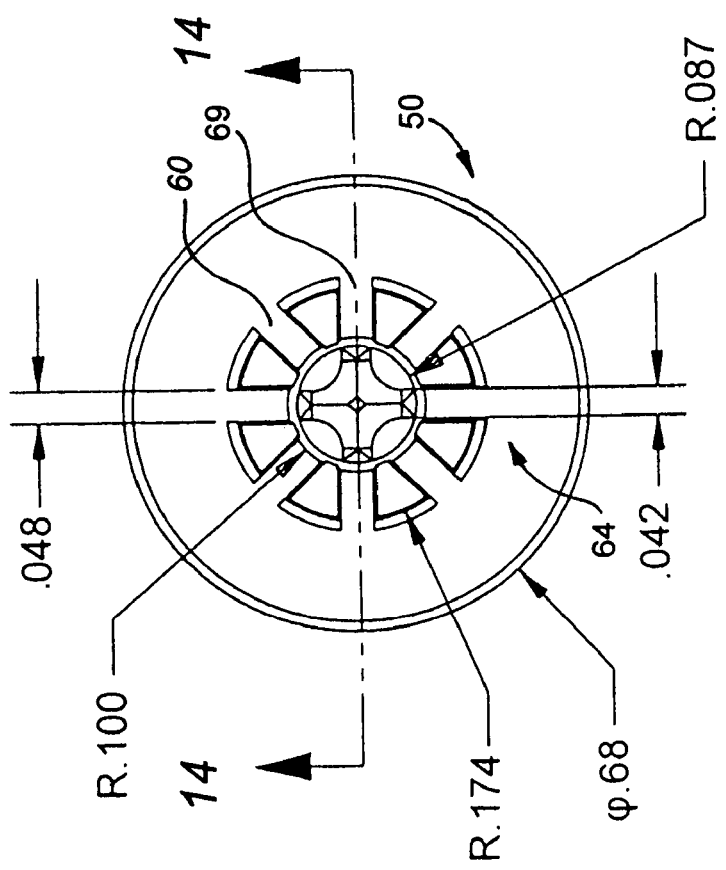
FIG. 12 is a top view illustrating a button constructed in accordance with the principles of the invention.

Possible different shapes 11A, 11B, 11C of plate 11 are illustrated in FIGS. 6 to 8, respectively. Plate 12 can also take on other shapes like, but not limited to, those illustrated in FIGS. 6 to 8.

Figure 2:
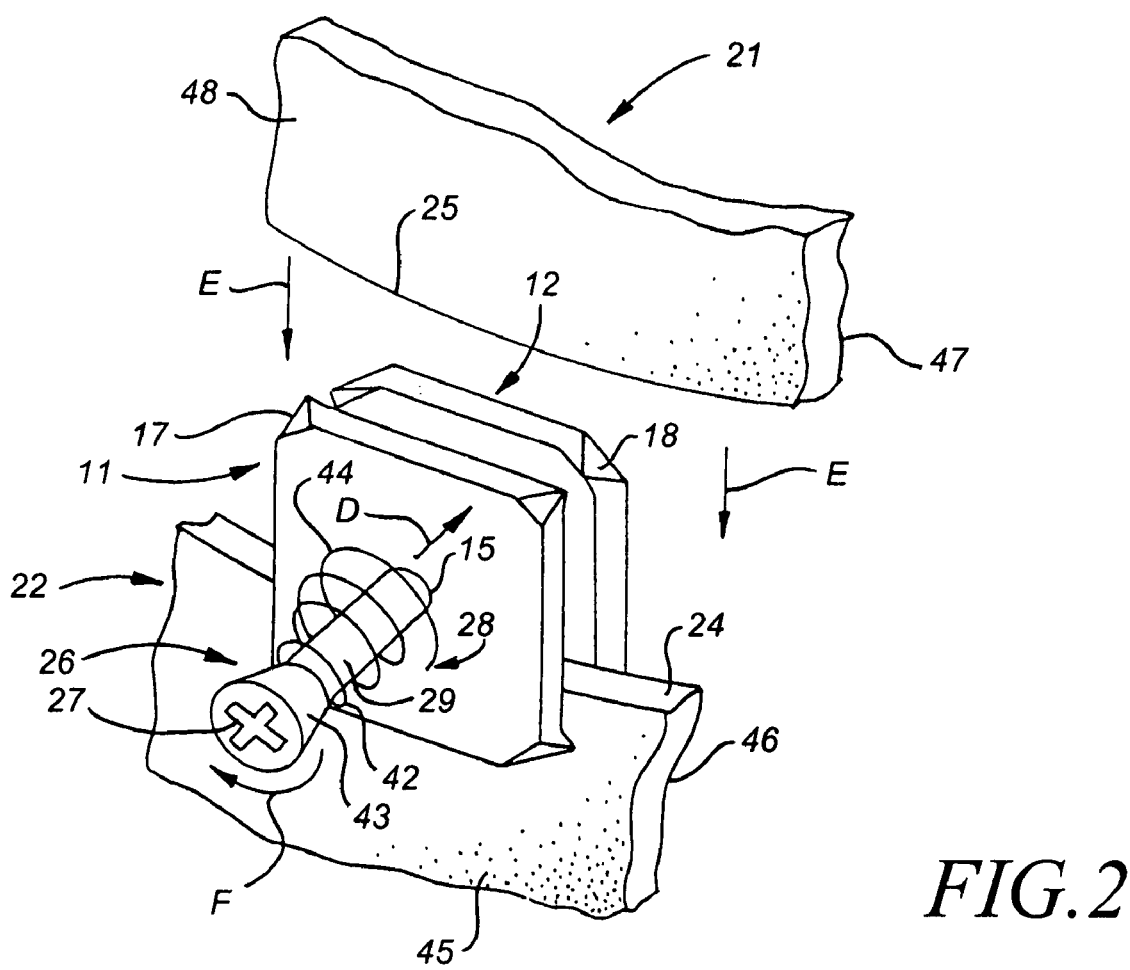
FIG. 2 is a perspective view illustrating the mode of operation of an improved Calvarian clamp constructed in accordance with the principles of the invention.
Figure 4:
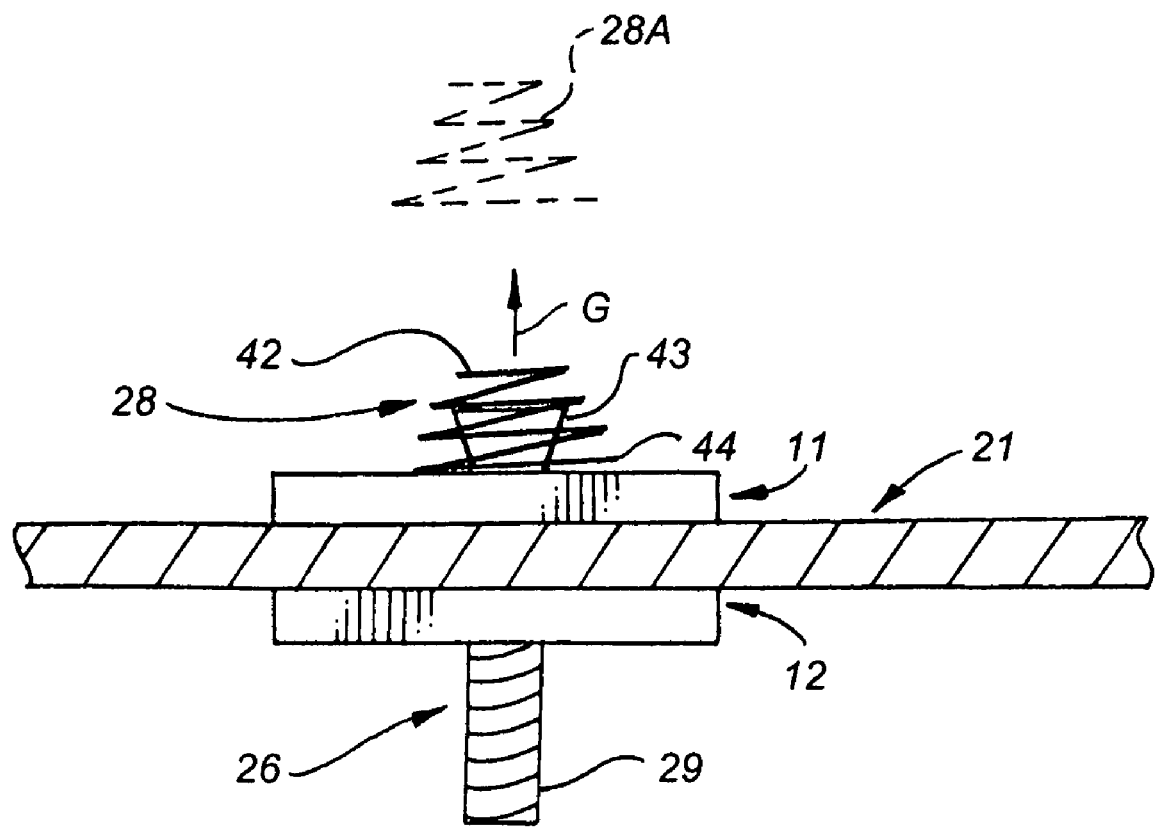
FIG. 4 is a side elevation view illustrating the mode of operation of the Calvarian clamp of the invention.
Figure 5:
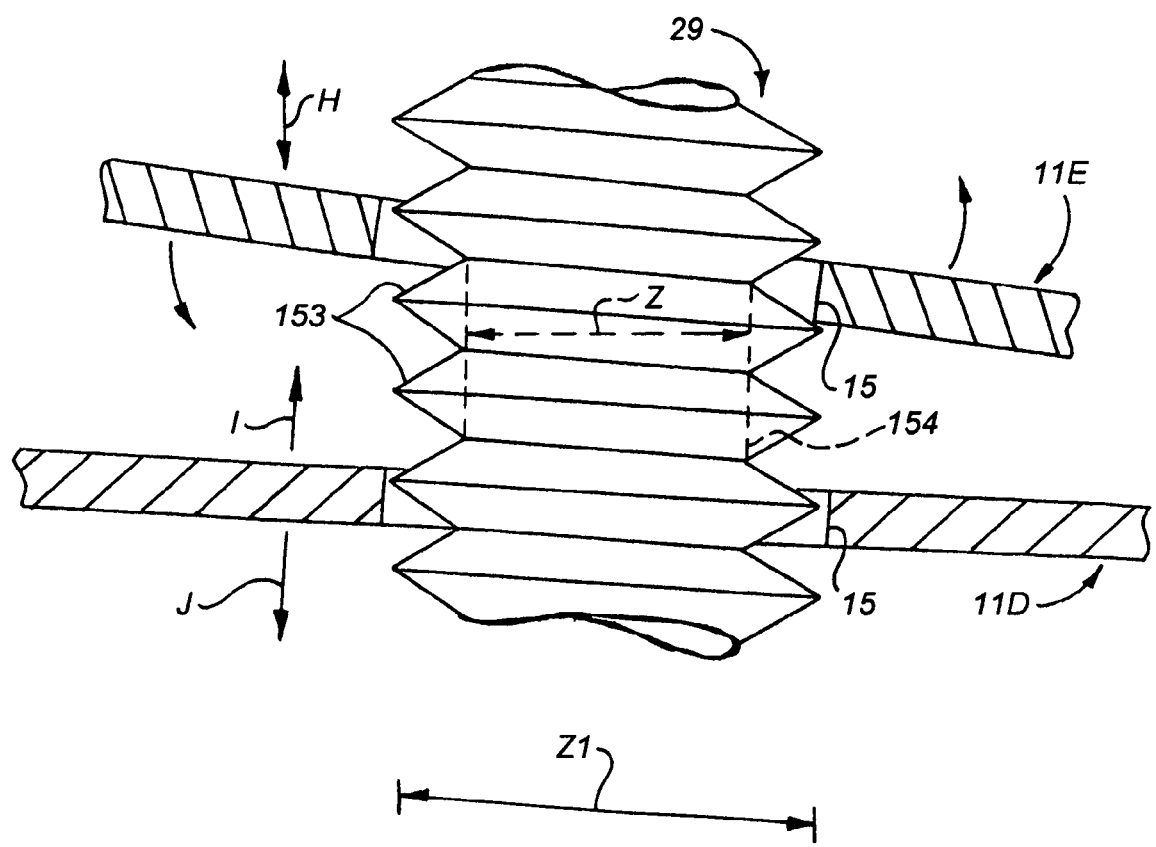
FIG. 5 is a partial side view of the Calvarian clamp of the invention illustrating the mode of operation thereof.

One embodiment of the improved clamp of the invention is illustrated in FIGS. 2, 4, and 5 and includes, as does the conventional clamp 10, plates 11 and 12. However, screw 13 is replaced with a screw 26 that includes a tapered head 26 provided with an opening 27 shaped to receive the tip of a Phillips or "star tip" screwdriver. In addition, the clamp of the invention includes a spring 28 that is interposed between head 43 and plate 11 (FIG. 2). The spring 28 can be cylindrical or any other shape, but is preferably conically shaped such that the top or smallest diameter portion 42 of spring 28 normally is not large enough (i.e., the inner diameter of the upper portion 42 of spring 28 is not large enough) for the upper portion 42 to slide over the head 43 of screw 26 and such that the lower part 44 of spring 28 (i.e., the inner diameter of the lower portion 44 of spring 28) is large enough to slide over the head 43. Consequently, when spring 28 is positioned around screw portion 29 in the manner shown in FIG. 2 and the distal end of screw 26 is slid through aperture 15 of plate 11 and turned into aperture 16 of plate 12 to the position shown in FIG. 2, and the plates are mounted on the edge 24 of bottom 22 of skull 23 in the manner shown in FIG. 2, spring 28 functions to press plate 11 against the outer surface 45 of bottom 22 and to draw plate 12 against the inner surface 46 of bottom 22 of skull 20. The top 21 of skull 20 is lowered in the direction of arrows E and worked between plates 12 and 13 and screw 11A is further turned into aperture 17 with a Phillips screwdriver to draw tightly plate 12 against the inner surfaces 47,46 of top 21 and bottom 22, respectively, of skull 20 and to compress plate 11 against the outer surfaces 48, 45 of top 21 and bottom 22, respectively of skull 20.

As screw 26 is turned with a Phillips screwdriver (the tip of which is inserted in opening 27 in head 43) in the direction of arrow E into aperture 17 in the direction of arrow D, head 43 compresses spring 28 against plate 11. Head 43 also forces the smaller diameter upper portion 42 of spring 28 over head 43 outwardly in the direction of arrow G (FIG. 4). After the smaller diameter upper portion 42 of spring 28 is forced over head 43, the remaining portion of spring 28 encircling head 24 has an inner diameter that is larger than the greatest outer diameter of tapered head 43. As a result, a technician can readily manually grasp and lift spring 28 off head 43 to the position indicated by dashed lines 28A in FIG. 4. The ability to remove spring 28 from head 43 is advantageous because after spring 28 is removed, if screw 26 is not turned in as far as possible into aperture 16 to force feet 17 and 18 into the bone, then screw 26 can be turned in the direction of arrow F to snug head 43 against plate 11 so the head 43 does not extend a great distance above plate 11. Tapered head 43 can, if desired, be sized such that the bottom narrower portion of head 43 seats in aperture 15, further reducing the distance the head 43 extends above plate 11.

As illustrated in FIG. 5, aperture 15 and the threads on portion 29 are shaped and dimensioned such that when plate 11 is tilted to a locked position in the manner indicated by reference character 11E in FIG. 5, aperture 15 engages or "catches" a thread portion and plate 11E is prevented from moving upwardly and downwardly in the directions indicated by arrows H. On the other hand, when plate 11 is positioned in a free sliding position normal to portion 29 in the manner indicated by reference character 11D in FIG. 5, aperture can freely slide upwardly in the direction of arrow I and downwardly in the direction of arrow J along portion 29. The ability of plate 11 to be positioned on portion 29 in both the locked position and the free sliding position is advantageous because when the clamp of the invention is initially positioned on the edge 24 of the bottom 22 of the skull, plate 11 can be manually grasped and tilted to the locked position on portion 29 such that plate 11 is spaced apart from the outer surface 45 of bottom 22. This facilitates positioning the edge 25 of top 21 between plates 11 and 12. After edge 25 is positioned between plates 11 and 12, plate 11 can be manually grasped and moved to the free sliding position normal to portion 29 such that spring 28 forces plate 11 toward and feet 17 against outer surface 45.

An alternate way to temporarily lock a plate 11B in position at a selected point on a screw 29 is to create auxiliary openings 15A, 15B that extend completely through plate 11B in the same manner that opening 15 extends completely through plate 11B, and that open at and extend to either side of cylindrical opening 15. See FIG. 7. At the same time, as illustrated in FIG. 5, a portion 15 of the threads of screw 29 are removed to produce a short section 154 of screw 29 that has a diameter that is indicated by arrows Z and that is less the width X (FIG. 7) of openings 15A and 15B. The width of openings 15A dn 15B is, however, less than the width Z1 (FIG. 5) of the threads of screws 29. Consequently, when plate 11B is aligned with section 154, plate 11B can be laterally displaced in the direction of arrows V, W so that a section 15A, 15B slides over section 154. When a section 15A, 15B is slid over section 154, plate 11B is prevented from moving up and down the threaded portion of screw 29 toward and away from the head of the screw 29. When it is desired to move plate 11B along the threaded portion of screw 29 toward or away from the head of screw 29, plate 11B is laterally displaced in the direction of arrow V, W to align and center opening 15 with the threaded portion of screw 29.

A seal or "trocar" button 50 constructed in accordance with the invention is illustrated in FIGS. 12 to 15. In FIGS. 12 to 15, the dimensions are in inches. During and prior to embalming openings are created in the abdominal cavity and possibly in soft tissue in the legs or other areas of the body where vascular distribution of embalming fluid may not be achieved. Openings may also be created in hard tissue. Openings can be formed using infant and standard sized needles, feeding tubes, drain tubes, IV main lines, pic lines, needle, etc. Button 50 functions to seal effectively a wide variety of such openings, regardless of the size of the opening.

The button 50 includes a head 64, an opening 61 extending into the center of button 50 to receive the tip of a Phillips screwdriver, external threads 51, and tip 65. Eight spaced apart fingers 60, 69 circumscribe and define the upper portion of opening 61. Opening 61 can, if desired, be formed to receive a flat blade on a screwdriver and/or to receive the end of any other tool than can be used to turn the button 50 into an opening formed in the epidermis, external integument, or soft tissue part of the body. Turning the button 50 into an opening 67 in tissue 66 seals the opening. After button 50 is turned into an opening 67 in tissue 66, the undersurface 68 of head 64 bears against tissue 66.

Figures 13, 14:
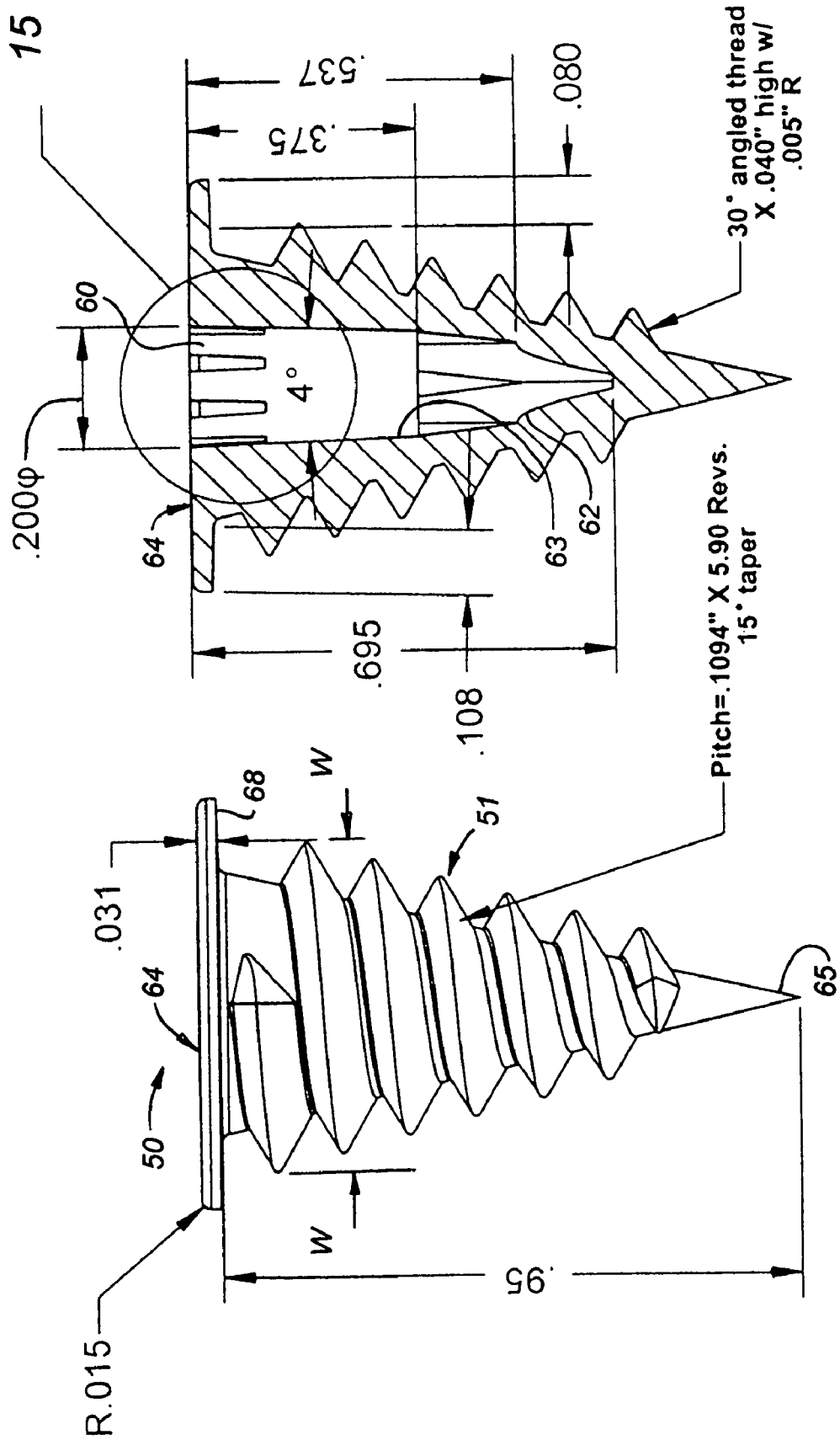
FIG. 13 is a side view illustrating further construction details of the button of FIG. 12.
FIG. 14 is a section view illustrating further construction details of the button of FIG. 13.

The length of button 50 is, as shown in FIG. 13, presently about 0.95 inch and is preferably in the range of 15 mm to 50 mm or more, most preferably 15 mm to 30 mm. Lengths less than 15 mm can be utilized but are not preferred in the practice of the invention.

Figure 16:
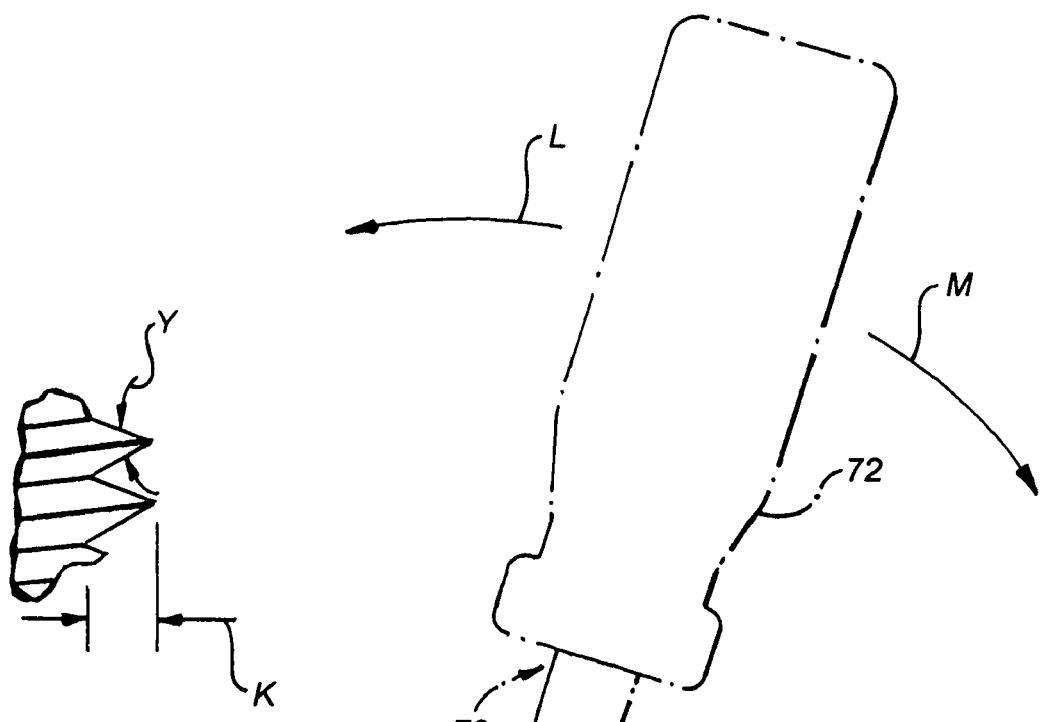
FIG. 16 is an enlarged view illustrating threads in the button of FIGS. 12 to 15.

The height of each thread 51 (or the depth of the valley between adjacent threads) is indicated by arrows K in FIG. 16 and is in the range of one to fifteen mm, preferably about two to four mm. Thread heights of less than one mm can be utilized but are not preferred in the practice of the invention because such threads do not appear effectively to seal an opening in the body. A "more aggressive" thread with a height in the range of one to fifteen mm is preferred in the invention, and is important in insuring that button 50 is not easily pulled free from an opening once the button is inserted.

The angle Y of a thread is less than 135 degrees, preferably less than 90 degrees, most preferably less than 45 or even 30 degrees. As the angle Y decreases, the ability of a thread 16, 17 to cut or extend into skin, muscle or other soft tissue and to engage the tissue improves. If, however, angle Y is too small, the thread begins to act like a knife and cust tissue. This appears to affect adversely the sealing ability of button 50. It is preferred that angle Y be at least fifteen degrees, preferably at least twenty degrees, most preferably at least thirty degrees.

Figure 17:
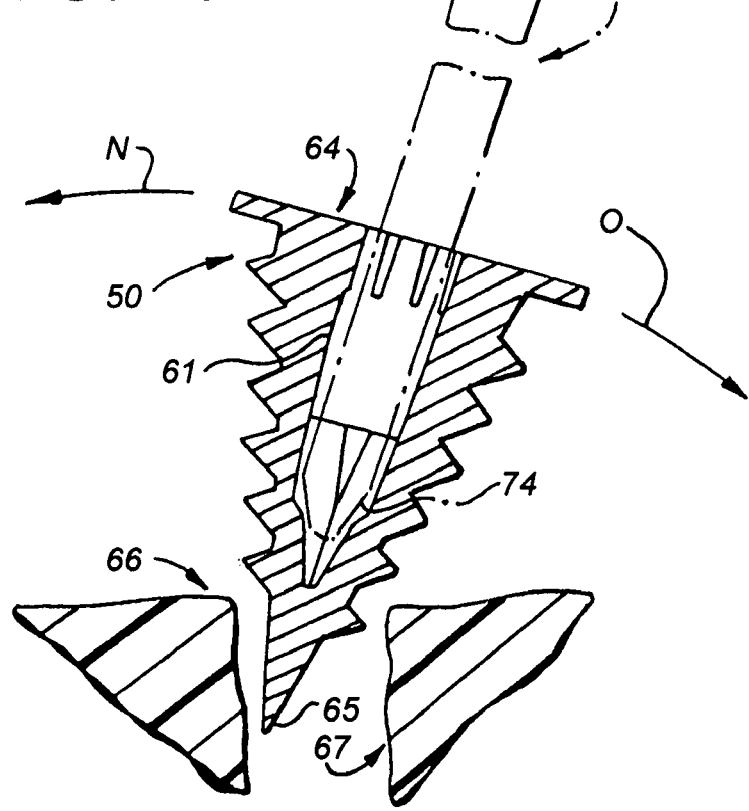
FIG. 17 is a side view illustrating the mode of operation of the button of FIGS. 12 to 15.

The greatest diameter of the threaded portion of button 50 is, as is indicated by arrows W in FIG. 13, about one-half inch. This diameter can vary and can be greater than one-half inch depending on the size opening 67 for which button 50 is intended. However, one advantage of the button 50 illustrated in FIGS. 12 to 15 is that it can be used in a wide variety of different sized openings 67, typically in the range of one-sixteenth to one-half inch wide. One reason button 50 fits in a wide variety of different sized openings is that the threads 51 have a height greater than one millimeter. Another reason is that the threads 51 extend nearly all the way to tip 65. A further reason is that the opening 61 extends far enough into button 50 so that a portion of the neck 73 above the "star-shaped" tip 74 of a screwdriver 71 extends into opening 61 in the manner illustrated in FIG. 17.

Opening 61 is shaped to receive a portion of neck 73 sufficient to cause a button 50 to move simultaneously with screwdriver 71. For example, if the screwdriver 71 is tilted in the direction of arrow L, button 50 simultaneously tilts in the direction indicated by arrow N. Or, if the screwdriver 71 is grasped by handle 72 and tilted in the direction of arrow M, button 50 simultaneously tilts in the direction indicated by arrow O. The ability to tilt button simultaneously with screwdriver 71 is important because it enables a user to control readily movement of button 50 and to insure that button 50 is being pressed into opening 67 in the desired direction of travel.

The distance between adjacent portions of thread 51 can vary as desired, i.e., the spiral path followed by the thread 51 on button 50 can be "stretched out" like a helical spring that is stretched, or, can be "tight" like a coil or helical spring that is tightly wound and has not been stretched.

Figure 18:
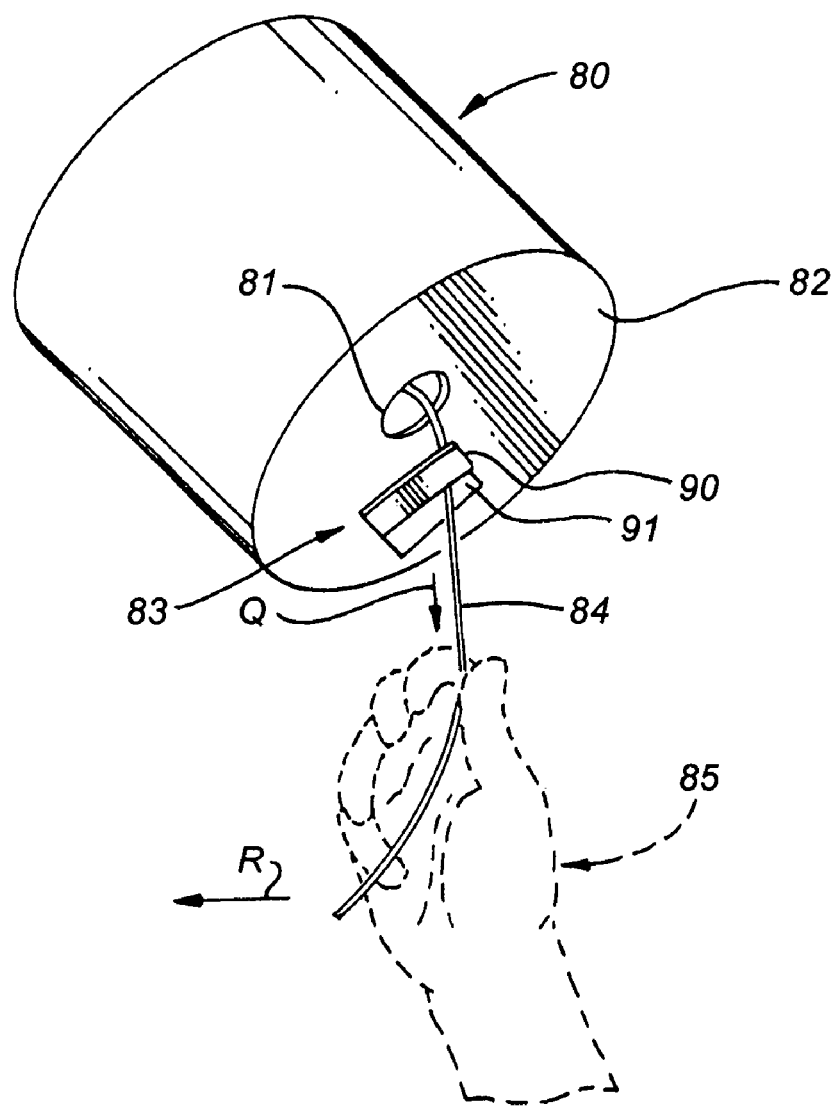
FIG. 18 is a perspective view illustrating a ligature dispenser constructed in accordance with the invention.

The ligature dispensing system illustrated in FIG. 18 includes a container enclosing a spool or other supply 86 of ligature (not visible in FIG. 18). One end of the ligature extends outwardly through an opening 81 formed in the top 82 of container 80. A slitted diaphragm or other means for engaging ligature can be placed over opening 81. A diaphragm or similar ligature engaging means is important because it allows ligature to be pulled outwardly in the direction of arrow Q and because it also prevents ligature from readily sliding through opening 81 back into container 80. When ligature 84 is manually 85 grasped and pulled out through opening 81, the ligature 84 is pulled through a cutter 83 and pulled in the direction of arrow R to force the ligature 84 between blades 90 and 91 to cut the ligature. In FIG. 18, cutter 83 is secured to top 82, but can if desired, be secured to the side of container 80, or to a support at some point remote from container 80.

Figure 19:
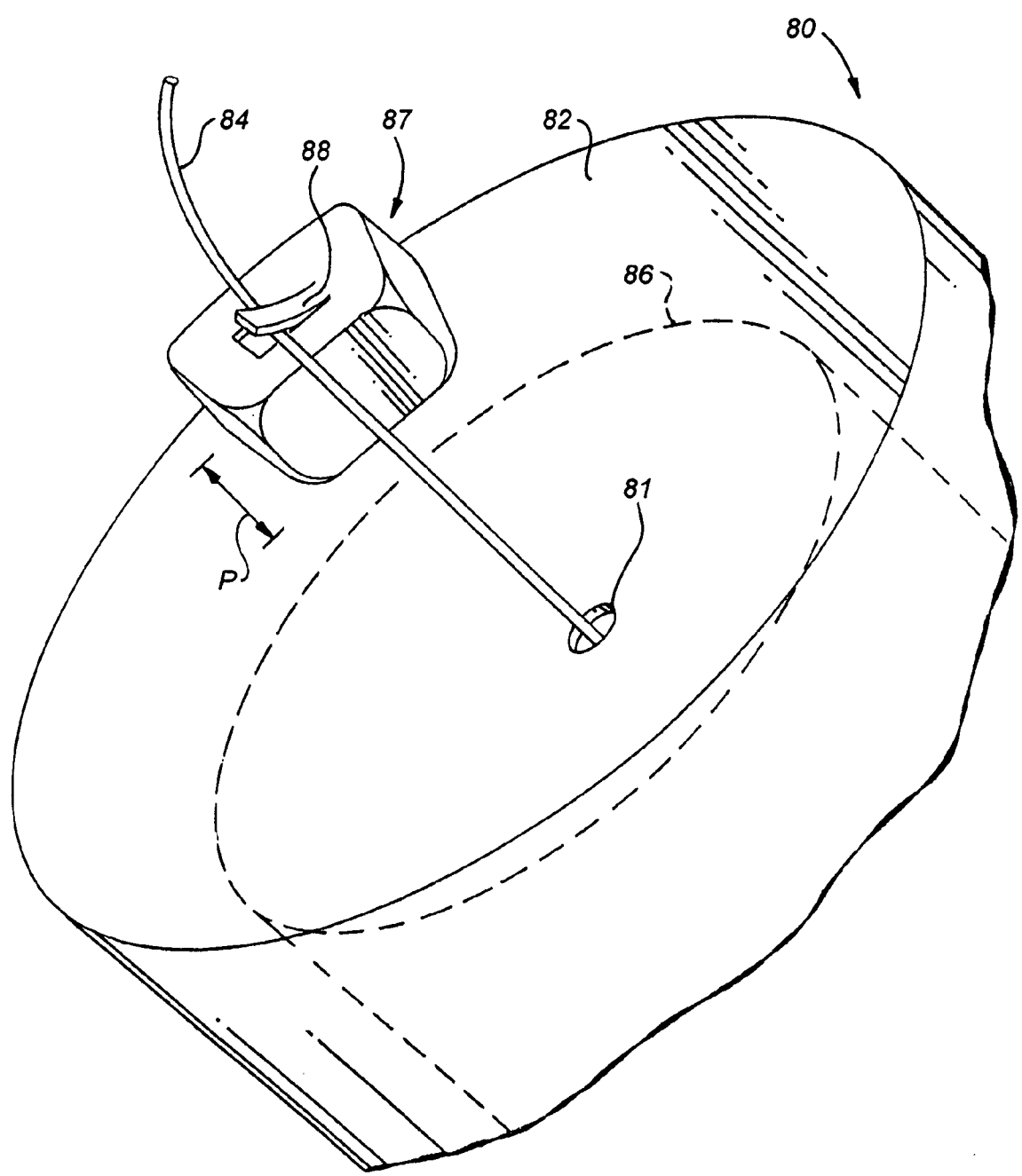
FIG. 19 is a perspective view illustrating another embodiment of the ligature dispenser of the invention.

An alternate embodiment of the ligature dispensing system is shown in FIG. 19 and includes the container 80, ligature spool 86, and opening 81 in the top 82 of the container 80. A different cutter 87 is secured to top 82. One valuable feature of cutter 87 is that the cutter blade 88 is positioned a distance P above the top 82 of container 80. Distance P is at least one-eighth of an inch, preferably at least one-quarter of an inch. Providing a cutter 87 or some other structural member that displaces ligature 84 a distance above top 82 after the ligature exits opening 81 is important because it makes grabbing ligature at a point intermediate opening 81 and cutter 87 much simpler, even when the user is wearing gloves. If ligature 84 is immediately adjacent top 82, it is difficult to grasp the ligature with the fingers of a gloved hand.

Placing ligature spool 86 in an enclosed container or at least behind a panel or some other shield is important because it functions to protect spool 86 from embalming fluid, bodily fluids and other contaminants that may be on the gloves of an embalmer and that may contact and contaminate the spool.

Figure 20:
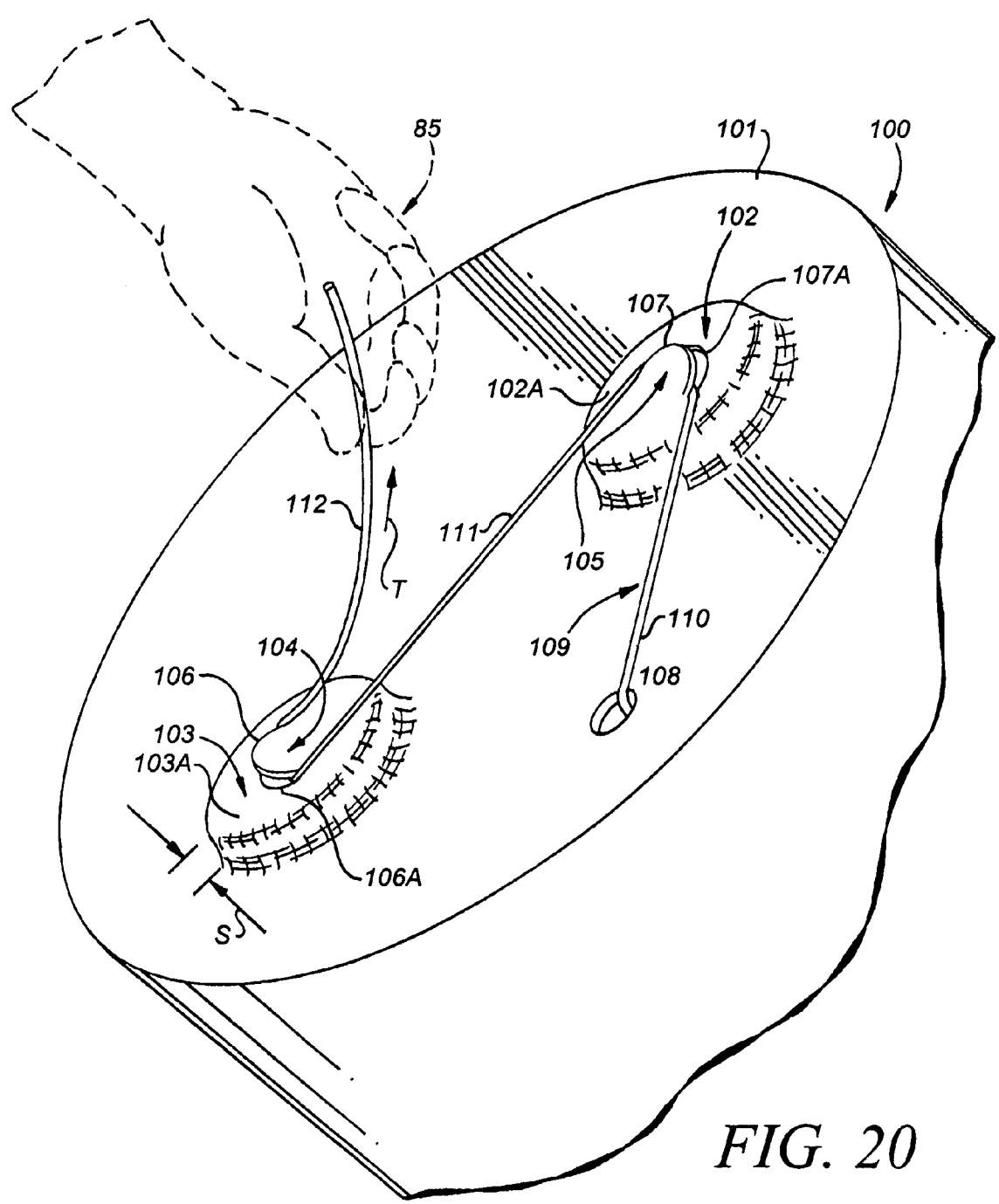
FIG. 20 is a perspective view illustrating a further embodiment of the ligature dispenser of the invention.

A further embodiment of the ligature dispensing system of the invention is shown in FIG. 20 and includes container 100, a ligature spool (not visible) in the container, and opening 108 formed in the top 101 of container 100. Raised areas or dimples 102 and 103 are formed in top 101. Area 103 includes circular upper surface 103A. Area 102 includes circular upper surface 102A. Each raised area 102,103 has an upraised arcuate cutter 105, 104, respectively, punched or otherwise formed therein. When cutter 104 is punched from area 103, semi-circular opening 106A is formed through area surface 103A. When cutter 105 is punched from area 102, semi-circular opening 107A is formed through surface 102A. Ligature 109 extends from the spool inside container 100 outwardly through opening 108 in the manner shown. Cutter 104 includes peripheral cutting edge 106. Cutter 105 includes peripheral cutting edge 107.

In use of the ligature dispensing system of FIG. 20, a length of ligature 109 is pulled outwardly from the ligature spool inside container 100 and through opening 108. The ligature is then wrapped around a cutter 105 and around a cutter 104 (or vice-versa) in the manner illustrated in FIG. 20. This produces a first length 110 of ligature extending from opening 108 to cutter 105, a second length 111 of ligature extending from cutter 105 to cutter 104, and a third end length 112 of ligature extending from cutter 104 to the hand 85 of the user. An individual uses his or her hand 85 to pull end length 112 in the direction of arrow T, causing edge 106 to cut the ligature 109 to free end length 112. After length 112 is cut free, lengths 111 and 110 normally remain in the positions illustrated in FIG. 20 until the user grasps length 111, unwraps and free ligature 109 from cutter 105, and pulls a desired length of ligature outwardly through opening 108 from the spool inside container 100. Once the user has pulled a desired length of ligature outwardly through opening 108, the user again wraps the ligature around cutters 105 and 104 (or vice-versa) and pulls on the end length of ligature that extends outwardly from cutter 104 to the hand 85 of the user. Pulling on the end length of ligature 109 causes edge 106 to sever ligature 109 and free said end length.

Figure 21:
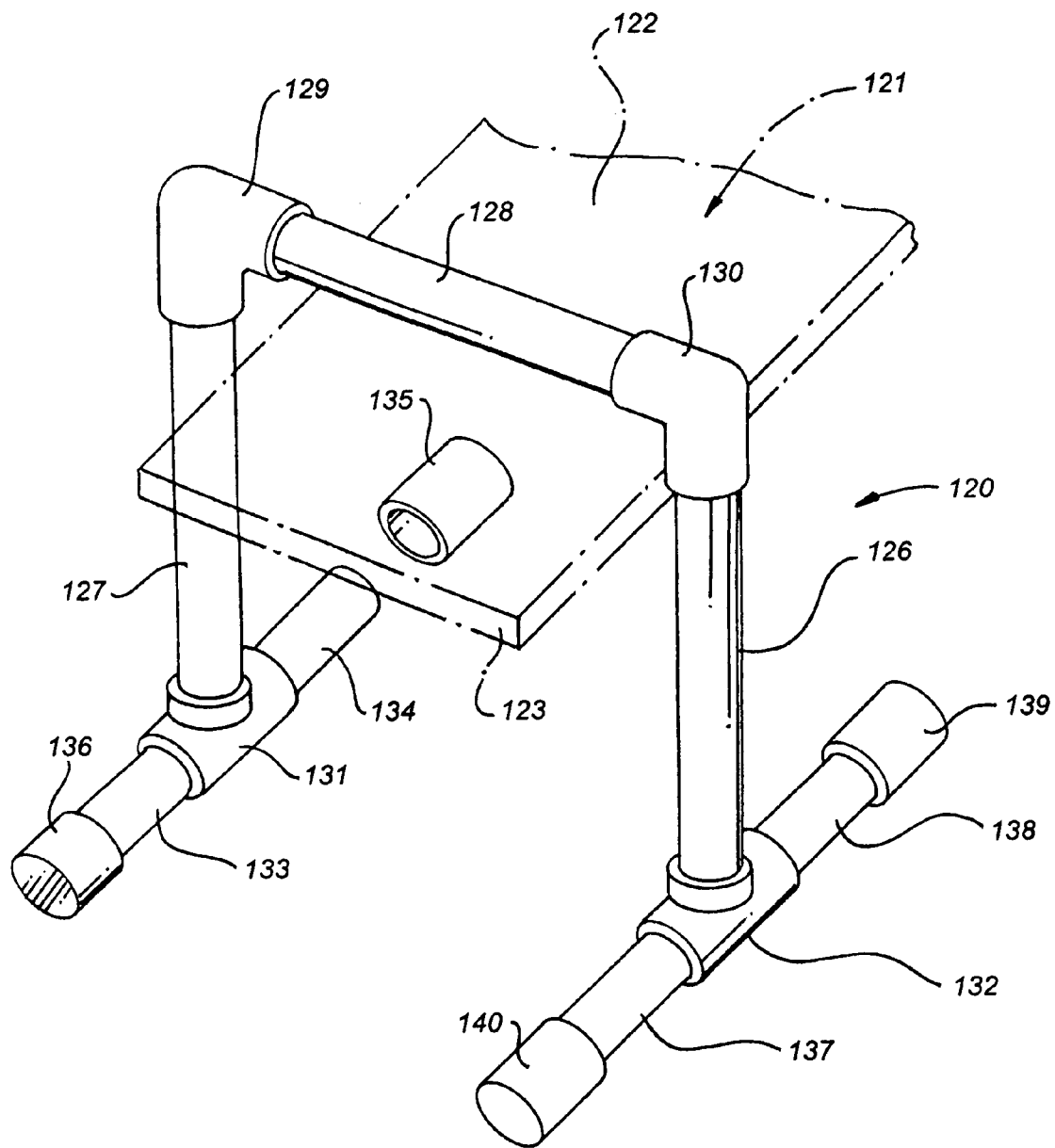
FIG. 21 is a perspective view illustrating an elevation apparatus constructed in accordance with the invention; and, FIG. 22 is an elevation view illustrating the mode of operation of the elevation apparatus of FIG. 21.

FIG. 21 illustrates an elevation device 120 constructed in accordance with the invention. Prior art leg elevation devices are set on the top 122 of a table 121 on which a deceased is being embalmed. Consequently, prior art leg elevation devices become contaminated with bodily fluids that may be on the top 122 of table 121. In contrast, device 120 does not contact top 122. Table 122 includes end 123.

While the construction of device 120 can vary as desired, the presently preferred construction is illustrated in FIG. 21 and includes legs 126 and 127, cross-bar 128, and foot members 133, 134, 137, 138. One end of cross-bar 128 slidably removably fits into L-shaped fitting 129. The other end of cross-bar 128 slidably removably fits into L-shaped fitting 130. The upper end of leg 127 slidably, removably fits into fitting 129. The upper end of leg 126 slidably, removably fits into fitting 130. The lower end of leg 127 slidably, removably fits into T-fitting 131. The lower end of leg 126 slidably, removably fits into T-fitting 132. One end of each foot 133,134 slidably removably fits into T-fitting 131. One end of each foot 137, 138 slidably removable fits into T-fitting 132. Cap 136 slidably removably fits on one end of foot 133. Cap 135 slidably removably fits on one end of foot 134. Cap 140 slidably removably fits on one end of foot 137. Cap 139 slidably removably fits on one end of foot 137. Device 120 is presently constructed from one and one-inch diameter PVC pipe. This size of pipe provides the necessary rigidity. One advantage of the device is that it is readily assembled for use and disassembled for storage. Another advantage of the device 120 is that the PVC pipe resists liquid absorption. As earlier noted, another important advantage of the device 120 is that it is not set on the top 122 of table during the embalming of a deceased.

Figure 22:
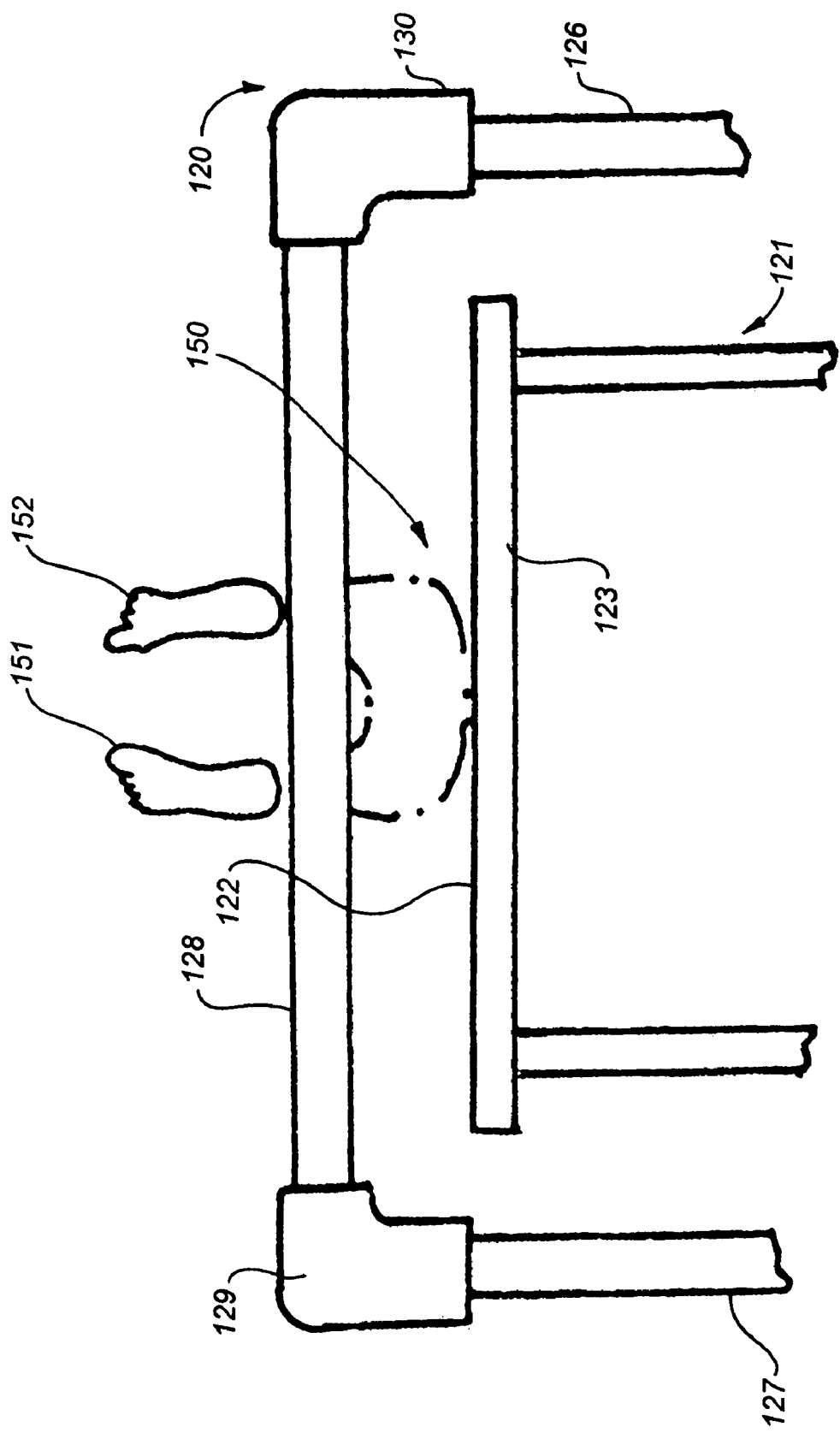

Use of elevation device 120 is illustrated in FIG. 22. After device 120 is assembled and placed adjacent table 121 in the manner illustrated in FIG. 22, the body 150 of a deceased individual is placed on top 122. The legs of body 150 are then elevated by positioning body 150 such that the Achilles tendons, or back portions of the ankles, rest on cross bar 128 in the manner illustrated in FIG. 22.

I have discovered a co-injection fluid used in the embalming process. The fluid facilitates embalming a deceased who have been refrigerated and who has blood coagulation. During the pre-embalming analysis, you determine how long the body has been refrigerated, the time of death, and the weight of the body. The fluid is used as a pre-inject or a co-inject. During a pre-inject, you pressurize the circulatory system in an individual that has not been refrigerated and that likely will experience significant blood clotting. The fluid is then injected. During a co-inject use of the fluid, the fluid is used simultaneously with some or all fluids during the embalming process. However, the fluid appears less effective with DODGE Plasdo 25 embalming fluid because it tends to produce some dehydration that produces visible dessication marks on the deceased. The fluid appears to be more effective when used in combination with METASYN, CHROMATECH (higher dye concentration), and INTROFIANT (tends to dehydrate more) embalming fluids produced by DODGE CHEMICAL CO. During a co-inject the fluid is mixed together with other embalming fluids prior to administration of the fluids in the body of the deceased.

The use of co-injection fluids functions to facilitates a more thorough distribution of embalming fluid throughout the body, decreases or eliminates the swelling that is so common with refrigerated bodies, and typically produces a skin condition in which the skin is more supple and soft without producing the dehydration that commonly occurs in a refrigerated body when it is embalmed. The co-injection fluid includes a defrigerant composition that promotes the foregoing functions.

By way of example, and not limitation, the average body (140 pounds) receives about 2.5 gallons of embalming fluid that is arterially injected. This 2.5 gallons (320 ounces) includes 12 ounces of defrigerant fluid, 16 ounces of restorative (humectant than includes oils because formaldehyde dehydrates a deceased's body), 32 ounces of METASYN (includes formaldehyde—about 18% formaldehyde), 32 ounces of METAFLOW (to break down blood clots), and 16 ounces of RECTIFIANT, the remainder of the 320 ounces being comprised of water.

If when embalming begins, it appears that the fluid is not distributing itself through the body as thoroughly as desired, the amount of defrigerant fluid in the embalming fluid can be increased. Normally the amount of defrigerant fluid will not exceed 128 ounces, preferably will not exceed 60 ounces, and most preferably will not exceed 24 ounces.

Normally in 320 ounces of embalming fluid there will at least four ounces of defrigerant fluid, preferably at least six ounces of defrigerant fluid, and most preferably at least eight ounces of defrigerant fluid. The defrigerant fluid does not have preservative qualities, it is used to alleviate hardening of the tissues, collapse of the blood vessels, and hardening of the tertiary spaces.

The defrigerant fluid can comprise methanol. Ethylene glycol and propylene glycol can also be utilized singly or in combination as the defrigerant fluid. Methanol and ethylene glycol are presently preferred. When, as noted above, twelve ounces of defrigerant fluid are utilized in 320 ounces of embalming fluid, the defrigerant fluid can comprise pure methanol or ethylene glycol, but the twelve ounces of defrigerant fluid typically comprises a mixture of methanol (or ethylene glycol) and water. The amount of water in the twelve ounces of defrigerant typically is about 40% to 60% by weight but can vary between five percent and ninety-five percent by weight.

The defrigerant fluid can be used in combination with water and formaldehyde. The defrigerant fluid normally is always administered to a deceased in combination with formaldehyde and water. However, the defrigerant fluid can be injected separately from (i.e., before or after) the formaldehyde. When the defrigerant is injected separately, the defrigerant fluid ordinarily is, as noted below, diluted with water.

Injecting the defrigerant fluid prior to injecting a formaldehyde solution in a deceased facilitates distribution of embalming fluid throughout the body. The defrigerant can be injected with water, with METAFLOW, or with any other desired co-injection fluids other than formaldehyde. The defrigerant fluid helps thaw the body and open blood vessels. When the defrigerant fluid is administered with water only, the defrigerant fluid typically comprises a solution of about 50% methanol (or ethylene glycol, etc) and 50% water. This 50-50 defrigerant fluid is typically further diluted by forming a solution that is 80% by volume of water and 20% by volume defrigerant fluid. For example, 100 ml of defrigerant fluid (which fluid consists of 50% methanol by volume and 50% water by volume) is admixed with 400 ml of water. It is possible to mix the defrigerant fluid (50% methanol and 50% water) to form a solution that is 50% by volume defrigerant fluid (50% methanol and 50% water) and 50% by volume water, but normally the defrigerant fluid (50% methanol and 50% water) is admixed with a sufficient amount of water to form a solution that includes at least 70% by weight water and 30% by weight of the defrigerant fluid. Using the defrigerant fluid (50% by volume methanol and 50% by volume water). The defrigerant fluid (50% methanol by volume and 50% water by volume) is not used without water, because severe dehydration results.

Having described in such terms as to enable those of skill in the art to make and practice it, and having described the presently preferred embodiments.

I claim:

1. A trocar button for insertion in an opening in soft tissue in the body of a deceased, said button comprising
   (a) a head (64), and,
   (b) a body
      (i) connected to, extending from, and tapering away from said head,
      (ii) having a distal tip (65) spaced away from said head,
      (iii) including an external thread
         having an angle Y of at least fifteen degrees,
         having a height K in the range of one to fifteen millimeters,
         having a maximum width W of about one-half inch, and
         extending substantially from said head to said tip, and
      (iv) having a length in the range of fifteen to fifty millimeters; and,
   (c) an opening (61) extending into said body to receive and engage an end of a tool used to turn the button in the opening in the body of a deceased.

2. A method for sealing an aperture in soft tissue in the body of a deceased, comprising the steps of
   (a) providing a tool having a distal tip, a handle, and a neck extending intermediate said tip and said handle;
   (b) providing a trocar button including
      (i) a head (64); and,
      (ii) a body
         connected to, extending from, and tapering away from said head, having a distal tip (65) spaced away from said head, including an external thread
            having an angle Y of at least fifteen degrees,
            having a height K in the range of one to fifteen millimeters,
            having a maximum width W of about one-half inch, and
            extending substantially from adjacent said head to said tip having a length in the range of fifteen to fifty millimeters; and,
      (iii) an opening (61) extending into said body to receive and engage said distal end of said tool to turn said tool to turn the button in the aperture in the body of a deceased;
   (c) inserting said distal tip in the aperture; and,
   (d) inserting said end of said tool in said opening and turning said tool to turn said body into the aperture to seal the aperture.

3. The button of claim 1 wherein said length of said body is about 0.95 inch.

4. The button of claim 1 wherein said height K is from about two to four millimeters.

5. The button of claim 1 wherein said angle Y is at least thirty degrees.

6. The button of claim 1 wherein said angle Y is less than forty five degrees.

7. The method of claim 2 wherein said length of said body is about 0.95 inch.

8. The method of claim 2 wherein said height K is from two to four millimeters.

9. The method of claim 2 wherein said angle Y is at least thirty degrees.

10. The method claim 2 wherein said angle Y is less than forty five degrees.

11. The method of claim 2 wherein said head has a thickness of 0.031 inch.

12. The method of claim 2 wherein a portion of said neck intermediate said tip and said handle extends into said opening such that during step (d) said button tilts simultaneously with said screwdriver and enables ready control of the movement of said button during insertion of said button.

13. The button of claim 1 wherein
   (a) said thread has a base and a spiral tip,
   (b) said thread has a surface that
      (i) slopes from said base away from said head, and
      (ii) extends from said base to said spiral tip along the entire length of said thread.

14. The button of claim 13 including a pointed conical tip.

* * * * *